(12) United States Patent
Sanborn et al.

(10) Patent No.: US 8,021,310 B2
(45) Date of Patent: Sep. 20, 2011

(54) WORK OF BREATHING DISPLAY FOR A VENTILATION SYSTEM

(75) Inventors: Warren G. Sanborn, Escondido, CA (US); Peter R. Doyle, Vista, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1425 days.

(21) Appl. No.: 11/408,457

(22) Filed: Apr. 21, 2006

(65) Prior Publication Data

US 2007/0272242 A1 Nov. 29, 2007

(51) Int. Cl.
*A61B 5/08* (2006.01)
(52) U.S. Cl. ......................................... 600/538; 600/529
(58) Field of Classification Search ........... 600/529–543
See application file for complete search history.

(56) References Cited

U.S. PATENT DOCUMENTS

| | | | |
|---|---|---|---|
| 3,703,893 A * | 11/1972 | Hardway, Jr. ................. | 600/538 |
| 5,107,830 A | 4/1992 | Younes .................... | 128/204.18 |
| 5,553,620 A | 9/1996 | Snider | |
| 5,606,976 A | 3/1997 | Marshall | |
| 5,730,140 A | 3/1998 | Fitch | |
| 5,881,723 A | 3/1999 | Wallace | |
| 5,884,622 A | 3/1999 | Younes .................... | 128/204.21 |
| 5,915,379 A | 6/1999 | Wallace | |
| 5,915,380 A | 6/1999 | Wallace | |
| 5,931,160 A | 8/1999 | Gilmore | |
| 5,975,081 A | 11/1999 | Hood | |
| 6,017,315 A | 1/2000 | Starr | |
| 6,024,089 A | 2/2000 | Wallace | |
| 6,118,847 A | 9/2000 | Hernandez-Guerra | |
| 6,158,432 A | 12/2000 | Biondi | |
| 6,240,920 B1 | 6/2001 | Strom | |
| 6,269,812 B1 | 8/2001 | Wallace | |
| 6,301,497 B1 | 10/2001 | Neustadter | |
| 6,305,373 B1 | 10/2001 | Wallace | |
| 6,339,410 B1 | 1/2002 | Milner | |
| 6,340,348 B1 | 1/2002 | Krishnan | |
| 6,342,040 B1 | 1/2002 | Starr | |
| 6,360,745 B1 | 3/2002 | Wallace | |
| 6,362,620 B1 | 3/2002 | Debbins | |
| 6,369,838 B1 | 4/2002 | Wallace | |
| 6,370,419 B1 | 4/2002 | Lampotang | |
| 6,377,046 B1 | 4/2002 | Debbins | |
| 6,390,091 B1 * | 5/2002 | Banner et al. ............ | 128/204.21 |
| 6,408,043 B1 | 6/2002 | Hu | |
| 6,488,029 B1 | 12/2002 | Hood | |
| 6,488,629 B1 | 12/2002 | Saetre | |
| 6,511,426 B1 | 1/2003 | Hossack | |
| 6,512,938 B2 | 1/2003 | Claure | |
| 6,533,723 B1 | 3/2003 | Lockery | |
| 6,543,449 B1 | 4/2003 | Woodring | |
| 6,544,192 B2 | 4/2003 | Starr | |

(Continued)

OTHER PUBLICATIONS

Cabello and Mancebo, Work of breathing, Intensive Care Med (2006) 32:1311-1314.*

(Continued)

*Primary Examiner* — Charles A Marmor, II
*Assistant Examiner* — Karen E Toth (57) ABSTRACT

A breathing support system is provided. The system may include a breathing support device configured to deliver gas to a patient and a display device associated with the breathing support device. The display device may be configured to display a work of breathing graphic indicating one or more work of breathing measures regarding the patient's breathing.

16 Claims, 5 Drawing Sheets

U.S. PATENT DOCUMENTS

| | | |
|---|---|---|
| 6,566,875 B1 | 5/2003 | Hasson |
| 6,584,973 B1 | 7/2003 | Biondi |
| 6,597,939 B1 | 7/2003 | Lampotang |
| 6,603,494 B1 | 8/2003 | Banks |
| 6,630,176 B2 | 10/2003 | Li |
| 6,650,346 B1 | 11/2003 | Jaeger |
| 6,668,829 B2 | 12/2003 | Biondi |
| 6,671,529 B2 | 12/2003 | Claure |
| 6,675,801 B2 | 1/2004 | Wallace |
| 6,679,258 B1 | 1/2004 | Strom |
| 6,707,476 B1 | 3/2004 | Hochstedler |
| 6,725,077 B2 | 4/2004 | Balloni |
| 6,733,449 B1 | 5/2004 | Krishnamurthy |
| 6,755,787 B2 | 6/2004 | Hossack |
| 6,782,888 B1 | 8/2004 | Friberg |
| 6,792,066 B1 | 9/2004 | Harder |
| 6,801,227 B2 | 10/2004 | Bocionek |
| 6,822,223 B2 | 11/2004 | Davis |
| 6,837,242 B2 | 1/2005 | Younes ............ 128/204.22 |
| 6,839,753 B2 | 1/2005 | Biondi |
| 6,899,103 B1 | 5/2005 | Hood |
| 6,932,767 B2 | 8/2005 | Landry |
| 6,956,572 B2 | 10/2005 | Zaleski |
| 6,970,919 B1 | 11/2005 | Doi |
| 7,017,574 B2 | 3/2006 | Biondi |
| 7,036,504 B2 | 5/2006 | Wallace |
| 7,039,878 B2 | 5/2006 | Auer |
| 7,062,251 B2 | 6/2006 | Birkett |
| 7,081,095 B2 | 7/2006 | Lynn |
| 7,117,438 B2 | 10/2006 | Wallace |
| 7,128,578 B2 | 10/2006 | Lampotang |
| 7,165,221 B2 | 1/2007 | Monteleone |
| 7,187,790 B2 | 3/2007 | Sabol |
| 7,188,621 B2 | 3/2007 | DeVries |
| 7,203,353 B2 | 4/2007 | Klotz |
| 7,223,965 B2 | 5/2007 | Davis |
| 7,246,618 B2 | 7/2007 | Habashi |
| 7,264,730 B2 | 9/2007 | Connell |
| 7,270,126 B2 | 9/2007 | Wallace |
| 7,278,579 B2 | 10/2007 | Loffredo |
| 7,294,112 B1 | 11/2007 | Dunlop |
| 7,300,418 B2 | 11/2007 | Zaleski |
| 7,303,680 B2 | 12/2007 | Connel |
| 7,318,892 B2 | 1/2008 | Connell |
| 7,333,969 B2 | 2/2008 | Lee |
| 7,334,578 B2 | 2/2008 | Biondi |
| 7,351,340 B2 | 4/2008 | Connell |
| 7,369,757 B2 | 5/2008 | Farbarik |
| 7,377,276 B2 | 5/2008 | Roy |
| 7,487,774 B2 | 2/2009 | Acker |
| 7,490,085 B2 | 2/2009 | Walker |
| 7,590,551 B2 | 9/2009 | Saleh |
| 2001/0056358 A1 | 12/2001 | Dulong |
| 2002/0044059 A1 | 4/2002 | Reeder |
| 2002/0077863 A1 | 6/2002 | Rutledge |
| 2002/0091548 A1 | 7/2002 | Auer |
| 2003/0062045 A1 | 4/2003 | Woodring |
| 2003/0208465 A1 | 11/2003 | Yurko |
| 2003/0230308 A1 | 12/2003 | Linden |
| 2004/0040560 A1* | 3/2004 | Euliano et al. ........ 128/204.23 |
| 2004/0059604 A1 | 3/2004 | Zaleski |
| 2004/0073453 A1 | 4/2004 | Nenov |
| 2004/0150525 A1 | 8/2004 | Wilson |
| 2004/0224293 A1 | 11/2004 | Penning |
| 2004/0249673 A1 | 12/2004 | Smith |
| 2005/0075904 A1 | 4/2005 | Wager |
| 2005/0085869 A1 | 4/2005 | Tehrani |
| 2005/0104860 A1 | 5/2005 | McCreary |
| 2005/0108057 A1 | 5/2005 | Cohen |
| 2005/0124866 A1 | 6/2005 | Elaz |
| 2005/0133027 A1 | 6/2005 | Elaz |
| 2005/0143632 A1 | 6/2005 | Elaz |
| 2005/0171876 A1 | 8/2005 | Golden |
| 2005/0188083 A1 | 8/2005 | Biondi |
| 2005/0215904 A1 | 9/2005 | Sumanaweera |
| 2005/0251040 A1 | 11/2005 | Relkuntwar |
| 2005/0288571 A1 | 12/2005 | Perkins |
| 2006/0078867 A1 | 4/2006 | Penny |
| 2006/0080140 A1 | 4/2006 | Buttner |
| 2006/0080343 A1 | 4/2006 | Carter |
| 2006/0144396 A1 | 7/2006 | DeVries |
| 2006/0149589 A1 | 7/2006 | Wager |
| 2006/0155183 A1 | 7/2006 | Kroecker |
| 2006/0174884 A1 | 8/2006 | Habashi |
| 2006/0195041 A1 | 8/2006 | Lynn |
| 2006/0213518 A1 | 9/2006 | DeVries |
| 2006/0229822 A1 | 10/2006 | Theobald |
| 2006/0264762 A1 | 11/2006 | Starr |
| 2007/0000490 A1 | 1/2007 | DeVries |
| 2007/0017515 A1 | 1/2007 | Wallace |
| 2007/0073181 A1 | 3/2007 | Pu |
| 2007/0113849 A1 | 5/2007 | Matthews |
| 2007/0156456 A1 | 7/2007 | McGillin |
| 2007/0157931 A1 | 7/2007 | Parker |
| 2007/0163589 A1 | 7/2007 | DeVries |
| 2007/0199566 A1 | 8/2007 | Be'eri |
| 2007/0229249 A1 | 10/2007 | McNeal |
| 2007/0241884 A1 | 10/2007 | Yamazaki |
| 2007/0271122 A1 | 11/2007 | Zaleski |
| 2007/0272241 A1 | 11/2007 | Sanborn |
| 2007/0272242 A1 | 11/2007 | Sanborn |
| 2007/0273216 A1 | 11/2007 | Farbarik |
| 2008/0000479 A1 | 1/2008 | Elaz |
| 2008/0007396 A1 | 1/2008 | Parkulo |
| 2008/0041380 A1 | 2/2008 | Wallace |
| 2008/0047554 A1 | 2/2008 | Roy |
| 2008/0053438 A1 | 3/2008 | DeVries |
| 2008/0065420 A1 | 3/2008 | Tirinato |
| 2008/0072896 A1 | 3/2008 | Setzer |
| 2008/0072901 A1 | 3/2008 | Habashi |
| 2008/0072902 A1 | 3/2008 | Setzer |
| 2008/0076992 A1* | 3/2008 | Hete et al. ............. 600/324 |
| 2008/0077033 A1 | 3/2008 | Figueiredo |
| 2008/0077436 A1 | 3/2008 | Muradia |
| 2008/0078390 A1 | 4/2008 | Milne |
| 2008/0091122 A1 | 4/2008 | Dunlop |
| 2008/0110460 A1 | 5/2008 | Elaz |
| 2008/0125873 A1 | 5/2008 | Payne |
| 2008/0172249 A1 | 7/2008 | Glaser-Seidnitzer |
| 2008/0178880 A1 | 7/2008 | Christopher |
| 2008/0178882 A1 | 7/2008 | Christopher |
| 2008/0183057 A1 | 7/2008 | Taube |
| 2008/0185009 A1 | 8/2008 | Choncholas |
| 2008/0205427 A1 | 8/2008 | Jost |
| 2008/0208012 A1 | 8/2008 | Ali |
| 2008/0214947 A1 | 9/2008 | Hunt |
| 2008/0236582 A1 | 10/2008 | Tehrani |
| 2008/0236585 A1 | 10/2008 | Parker |
| 2008/0251070 A1 | 10/2008 | Pinskiy |
| 2008/0255880 A1 | 10/2008 | Beller |
| 2008/0258929 A1 | 10/2008 | Maschke |
| 2008/0293025 A1 | 11/2008 | Zamierowsi |
| 2008/0295830 A1 | 12/2008 | Martonen |
| 2008/0312954 A1 | 12/2008 | Ullrich |
| 2008/0319513 A1 | 12/2008 | Pu |
| 2009/0005651 A1 | 1/2009 | Ward |
| 2009/0054743 A1 | 2/2009 | Stewart |
| 2009/0055735 A1 | 2/2009 | Zaleski |
| 2009/0062674 A1* | 3/2009 | Jin et al. ............. 600/529 |
| 2009/0063181 A1 | 3/2009 | Nho |
| 2009/0125333 A1 | 5/2009 | Heywood |
| 2009/0126734 A1 | 5/2009 | Dunsmore |
| 2009/0131758 A1 | 5/2009 | Heywood |
| 2009/0149200 A1 | 6/2009 | Jayasinghe |
| 2009/0149927 A1 | 6/2009 | Kneuer |
| 2009/0150184 A1 | 6/2009 | Spahn |
| 2009/0159082 A1* | 6/2009 | Eger ............. 128/204.23 |
| 2009/0209849 A1 | 8/2009 | Rowe |
| 2009/0221926 A1 | 9/2009 | Younes |
| 2009/0229611 A1* | 9/2009 | Martin et al. ........ 128/204.21 |
| 2009/0240523 A1 | 9/2009 | Friedlander |
| 2009/0241952 A1 | 10/2009 | Nicolazzi |
| 2009/0241956 A1 | 10/2009 | Baker, Jr. |
| 2009/0241957 A1 | 10/2009 | Baker, Jr. |
| 2009/0241958 A1 | 10/2009 | Baker, Jr. |
| 2009/0244003 A1 | 10/2009 | Bonnat |
| 2009/0250054 A1 | 10/2009 | Loncar |

OTHER PUBLICATIONS

MA Banner, RR Kirby, A Gabrielli, PB Blanch, AJ Layon. Partially and Totally Unloading Respiratory Muscles Based on Real-Time Measurements of Work of Breathing: A Clinical Approach; Chest 1994; 106; 1835-1842.*

* cited by examiner

WORK OF BREATHING DISPLAY FOR A VENTILATION SYSTEM

TECHNICAL FIELD

The present disclosure relates generally to the field of respiratory support, and more particularly to a graphical display indicating work of breathing measures.

BACKGROUND

One indication of a patient's condition during respiration support is the status of the patient's work of breathing (WOB). Work of breathing may be defined as the work associated with inflating the patient's lungs during a breathing cycle. During respiration support, a ventilator provides at least a portion of the total work of breathing for the patient. The total work of breathing ($WOB_{TOTAL}$) may generally be defined as the sum of the work of breathing provided by the patient ($WOB_{PATIENT}$) and the work of breathing support provided by the ventilator ($WOB_{VENTILATOR}$).

The work of breathing provided by the patient ($WOB_{PATIENT}$) may be approximated as the sum of two components: an elastic WOB component ($WOB_{PATIENT-ELASTIC}$) and a resistive WOB component ($WOB_{PATIENT-RESISTIVE}$). The elastic WOB component is generally defined as the work required to overcome the elastance of the patient's respiratory system, while the resistive component is generally defined as the work required to overcome the airway resistance of the patient's respiratory system.

Elastance may generally be defined in terms of the elastic properties of the lung and chest, or the forces associated with expanding the lung. In particular, the degree of stiffness of the lung-chest region may be referred to as the elastance of the respiratory system. The elastance of the respiratory system may also be discussed in terms of compliance, which may be defined as the inverse of elastance. Generally, the easier it is to stretch the lung-chest region.

Resistance forces, or the non-elastic forces at work in the breathing cycle, are the forces associated with moving air through a patient's airways. Lung resistance may be at least partially defined by a patient's physiological conditions. For example, patients suffering from asthma typically experience muscular constriction of the bronchi. Such patients may also experience swelling of the bronchial mucosa. The work required to achieve a particular amount of air flow through the breathing passageways generally increases in proportion to the severity of constriction. In some ventilation systems, flow and pressure sensors are used to compute estimates of the patient's resistance and compliance.

One or more WOB values, e.g., the total WOB, the patient's WOB ($WOB_{PATIENT}$), the ventilator's WOB ($WOB_{VENTILATOR}$), the elastic WOB component ($WOB_{PATIENT-ELASTIC}$), and/or the resistive WOB component ($WOB_{PATIENT-RESISTIVE}$) may be determined and/or monitored in various manners. For example, a patient's WOB may be determined from either measured or estimated values relating to the patient's respiratory physiology by applying direct or indirect approaches and following established algorithms. Measured values may be obtained more directly by invasive procedures, e.g., procedures that require the installation of an esophageal balloon. Such techniques are typically invasive and require specialized skill. Thus, outside of the research setting it may be undesirable to obtain WOB measures employing such invasive means.

In a pressure assisted ventilation (PAV) system, the patient's work of breathing ($WOB_{PATIENT}$), the elastic WOB component ($WOB_{PATIENT-ELASTIC}$), and/or the resistive WOB component ($WOB_{PATIENT-RESISTIVE}$) may be estimated by inputting measurements from various sensors into the breathing algorithms. In PAV ventilation, the patient is supplied with continuous pressure assistance throughout an inspiratory effort and in direct proportion to the moment-to-moment inspiratory effort. Typically, none of the instantaneous inspiratory pressure, the instantaneous flow, or the resulting volume are set by the caregiver. Because the PAV breathing algorithm harmoniously links the ventilator to the patient, the patient effectively "drives" the ventilator. By appropriately setting the value of the proportionality (% support) control, the caregiver may effectively partition the total WOB between the patient ($WOB_{PATIENT}$) and the ventilator ($WOB_{VENTILATOR}$).

The values of the patient's lung-chest compliance and lung resistance may be continuously estimated and inserted into the PAV breathing algorithm in order for the algorithm to function properly. These estimates may be made automatically by the ventilator and fed back to the breathing algorithm as perhaps better fits the needs of the patient in intensive care, whereas manual techniques may be used to estimate the values for more stable patients, e.g., in a home setting.

SUMMARY

In accordance with the present disclosure, systems and methods for monitoring and/or displaying one or more work of breathing measures are provided.

According to one embodiment, a breathing support system is provided. The system may include a breathing support device configured to deliver gas to a patient and a display device associated with the breathing support device. The display device may be configured to display a work of breathing graphic indicating one or more work of breathing measures regarding the patient's breathing.

According to another embodiment, a device for displaying work of breathing information associated with a breathing support system is provided. The device may include a work of breathing calculation module configured to determine one or more work of breathing measures regarding a patient's breathing, and a display configured to present a work of breathing graphic indicating the one or more determined work of breathing measures.

According to yet another embodiment, a method for displaying a work of breathing graphic associated with a breathing support system is provided. The method may include calculating one or more work of breathing measures regarding a patient's breathing, and displaying a work of breathing graphic indicating the one or more calculated work of breathing measures.

According to yet another embodiment, a ventilation system for assisting with a patient's breathing is provided. The system may include gas delivery means for delivering gas to a patient, and display means for displaying a work of breathing graphic that indicates one or more work of breathing measures regarding the patient's breathing.

According to yet another embodiment, a computer-readable medium including computer-executable instructions for providing a work of breathing graphic associated with breathing support for a patient is provided. The computer-executable instructions may include instructions for calculating one or more work of breathing measures regarding a patient's breathing, and instructions for displaying a work of breathing graphic indicating the one or more calculated work of breathing measures.

BRIEF DESCRIPTION OF THE DRAWINGS

Some embodiments of the disclosure may be understood by referring, in part, to the following description and the accompanying drawings, in which like reference numbers refer to the same or like parts, and wherein.

DETAILED DESCRIPTION

Selected embodiments of the disclosure may be understood by reference, in part, to FIGS. 1-9, wherein like numbers refer to same and like parts.

In general, the present disclosure describes generating and/or displaying a work of breathing graphic (WOB graphic) for use with a ventilator or other breath delivery or breathing support system that may provide caregivers with various information concerning work of breathing through an easily understood graphical display. The WOB graphic may be used, e.g., for monitoring and/or adjusting the amount of work of breathing contributed by the patient and/or the amount contributed by the ventilator. For example, the display may allow a caregiver to monitor a patient's work of breathing in real time or substantially in real time. A caregiver may use such information for various purposes, such as, for example, to ensure that the patient's work of breathing is within a safe or desirable range and/or to determine whether and/or how to adjust one or more ventilator settings (e.g., to increase or decrease respiratory support to the patient).

In some embodiments, the WOB graphic may depict (graphically, numerically, or otherwise) the effect that changes in one or more ventilator settings have on the work of breathing being contributed by a patient, e.g., in order to determine whether or not such adjustments are causing a patient to work at a level above, within, or below an acceptable or desired range of work. The WOB graphic may be user-friendly such that caregivers of various degrees of technical sophistication may understand or interpret the display and/or be able to utilize the display for implementing or managing a respiration support strategy. Additionally, the WOB graphic may be used in conjunction with traditional ventilation systems and applications, e.g., pressure assisted ventilation (PAV) applications.

The WOB graphic may be displayed via any of a variety of media. For example, in some embodiments, the WOB graphic may be displayed by a ventilator or a ventilator control system. In other embodiments, the WOB graphic may be displayed on a separate display device (e.g., separate from a ventilator). In particular embodiments, the WOB graphic may be displayed in association with a ventilation control system for administering a respiration support strategy. In such embodiments, a ventilator may be connected to a graphic user interface having a digital processor, a display screen, and/or one or more user inputs, or the ventilator may itself include a graphic user interface. These components may cooperate to assist a caregiver in setting up and/or adjusting the work of breathing being provided by a patient and/or the work of breathing being provided the ventilator.

In some embodiments, the WOB graphic may indicate the total work of breathing ($WOB_{TOTAL}$), the patient's work of breathing ($WOB_{PATIENT}$) (neither or which, one or which, or both of which advance or retreat along a scale) and/or the components of the patient's WOB—an elastic WOB component ($WOB_{PATIENT-ELASTIC}$) and a resistive WOB component ($WOB_{PATIENT-RESISTIVE}$). For example, the WOB graphic may include a $WOB_{TOTAL}$ graphic or indicator that that indicates the total work of breathing, a $WOB_{PATIENT}$ graphic or indicator that that indicates the patient's work of breathing, and an elastic-resistive WOB graphic that indicates a measure of the elastic WOB component ($WOB_{PATIENT-ELASTIC}$) relative to a measure of the resistive WOB component ($WOB_{PATIENT-RESISTIVE}$). As another example, the WOB graphic may include a $WOB_{TOTAL}$ graphic or indicator that that indicates the total work of breathing, a $WOB_{PATIENT}$ graphic or indicator that that indicates the patient's work of breathing, an elastic WOB graphic that indicates a measure of the elastic WOB component ($WOB_{PATIENT-ELASTIC}$), and a resistive WOB graphic that indicates a measure of the resistive WOB component ($WOB_{PATIENT-RESISTIVE}$). In other embodiments, one or more additional and/or other components of a total work of breathing measure may be displayed, e.g., the ventilator work of breathing ($WOB_{VENTILATOR}$).

In some embodiments, the WOB graphic may include a scale having any suitable shape and configuration (e.g., a linear scale, a circular or semicircular scale, or an elliptical scale) and one or more indicators that move relative to the scale to indicate one or more work of breathing parameters. For example, the WOB graphic may include a first indicator that moves relative to the scale to represent a measure of $WOB_{TOTAL}$, and a second indicator that moves relative to the scale to represent a measure of $WOB_{PATIENT}$. The scale may be divided into sectors that generally correspond to different work of breathing levels. The sectors may be visibly discernable from each other (or at least from immediately adjacent sectors). For example, the sectors may be color-coded or distinctively shaded.

An elastic-resistive WOB graphic may be divided into a first portion and a second portion, the first portion indicating the elastic WOB component ($WOB_{PATIENT-ELASTIC}$) and the second portion indicating the resistive WOB component ($WOB_{PATIENT-RESISTIVE}$). The relative sizes of the first and second portions of the elastic-resistive WOB graphic may dynamically adjust to indicate the measure of the elastic WOB component relative to the measure of the resistive WOB component. In certain embodiments, the overall size of the elastic-resistive WOB graphic remains constant as the relative sizes of the first and second portions dynamically adjust.

Figure 1:
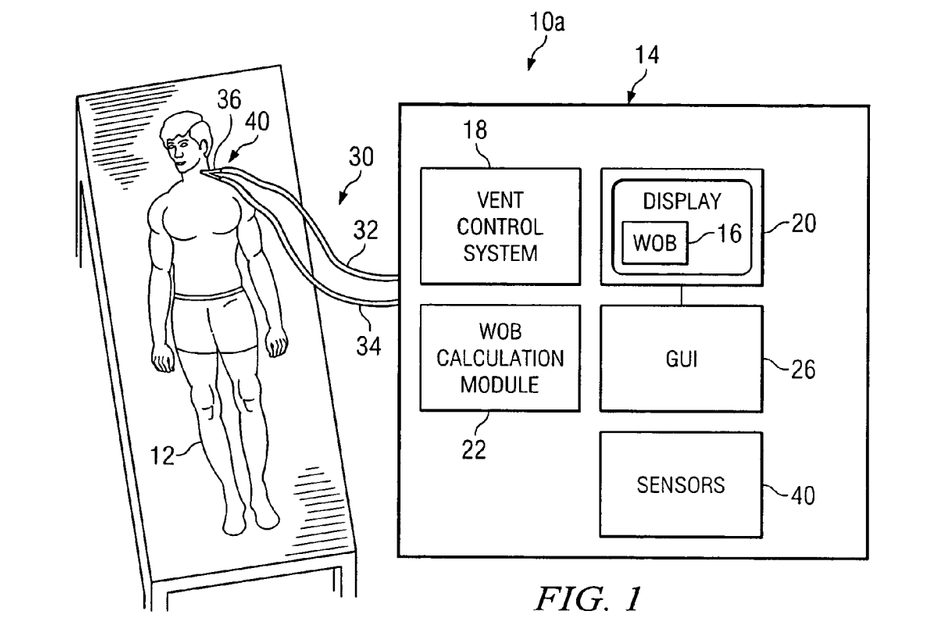
FIG. 1 illustrates a ventilation system for providing ventilation support to a patient, including a ventilator configured to display a work of breathing graphic, according to one embodiment of the disclosure.
Figure 2:
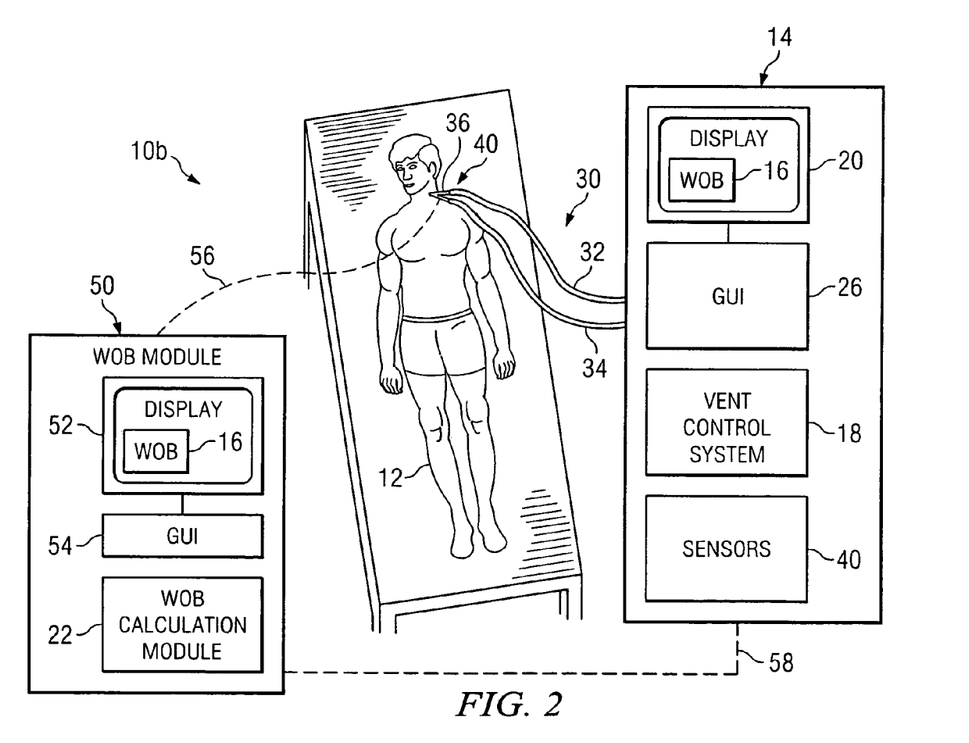
FIG. 2 illustrates a ventilation system for providing ventilation support to a patient, including a ventilator and a separate module for displaying a work of breathing graphic, according to one embodiment of the disclosure.

FIGS. 1 and 2 illustrate two example embodiments of a ventilation system including a displayed WOB graphic. More particularly, FIG. 1 illustrates an example ventilation system including a ventilator configured to display a work of breathing graphic, while FIG. 2 illustrates an example ventilation system including a ventilator and a separate module for displaying a work of breathing graphic.

Referring to FIG. 1, a ventilation system 10a for providing breathing assistance to a patient 12 may include a ventilator 14 configured to display a WOB graphic 16 and one or more devices for connecting ventilator 14 to patient 12. As used throughout this document, the term "ventilator" may refer to any device, apparatus, or system for delivering breathing gas to a patient, e.g., a ventilator, a respirator, a CPAP device, or a BiPAP device. The term "patient" may refer to any person who is receiving breathing support from a ventilation system, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Ventilator 14 may include a ventilation control system 18, a display device 20, and a WOB calculation module 22. Ventilation control system 18 may be operable to control the ventilation support provided by ventilator 14 based on various inputs, such as inputs received from an operator and/or data received from various sensors, as discussed below. Display device 20 may be fully or partially integrated with ventilator 14 and may comprise, e.g., a touch screen display or other visual display. Display device 20 may be configured to display various information regarding the ventilation of patient 12, including WOB graphic 16 and/or other information regarding the ventilation of patient 12 (e.g., tidal volume, minute ventilation, and respiration rate). WOB graphic 16 may display one or more work of breathing measures in any suitable manner, e.g., graphically, numerically, or otherwise. WOB graphic 16 may be a full screen display or may occupy a portion of a display screen. For example, WOB graphic 16 may be located in a window or a portion of a display that includes other information regarding the ventilation of patient 12.

Display device 20 may be part of or otherwise associated with, a graphic user interface 26. In this embodiment, graphic user interface 26 may be configured to display WOB graphic 16 and/or other information via display device 20 and/or provide an interface for accepting input from human operators via display device 20 and/or other input devices (e.g., to set or modify ventilation settings, to access data, and/or to change or configure the display).

Patient 12 may be connected to ventilator 14 by a breathing circuit 30 that may include an inspiration conduit 32, an exhalation conduit 34, and/or a patient connection apparatus 36. Patient connection apparatus 36 may include any device or devices configured to connect breathing circuit 30 to one or more breathing passageways of patient 12. For example, patient connection apparatus 36 may include a patient connection tube directly connected to the patient's trachea, an artificial airway (e.g., an endotracheal tube or other device) inserted in the patient's trachea, and/or a mask or nasal pillows positioned over the patient's nose and/or mouth. In embodiments including a patient connection tube, the patient connection tube may include a Wye (or "Y") connector.

Ventilation system 10a may include one or more sensors 40 for sensing, detecting, and/or monitoring one or more parameters related to the ventilation of patient 12, e.g., parameters regarding the ventilation provided by ventilator 14 and/or physiological parameters regarding patient 12. For example, sensors 40 may include one or more devices for measuring various parameters of gas flowing into or out of patient 12 or ventilator 14, e.g., the pressure, flow rate, flow volume, temperature, gas content, and/or humidity of such gas flow. Thus, sensors 40 may include, e.g., one or more pressure sensors, flow meters, transducers, and/or oxygen sensors. Sensors 40 may be located at one or more various locations in ventilation system 10a for monitoring the pressure and or flow of gasses flowing into and/or out of patient 12 and/or ventilator 14. For example, one or more sensors 40 may be located in or proximate ventilator 14, breathing circuit 30, and/or patient connection apparatus 36. For example, depending on the particular embodiment, one or more sensors 40 may be located within or proximate to ventilator 14, inspiration conduit 32 and/or exhalation conduit 34 or breathing circuit 30, an artificial airway, and/or a Wye connector.

As discussed above, ventilation control system 18 may be operable to control the ventilation support provided by ventilator 14 based on various input received from an operator (e.g., via graphic user interface 26 and/or other user interfaces on ventilator 14) and/or data received from one or more sensors 40. For example, ventilation control system 18 may regulate the pressure and/or flow of gas delivered to a patient based at least on data received from sensors 40.

WOB calculation module 22 may be operable to calculate or otherwise determine one or more work of breathing measures based on various input data, including data collected by sensors 40, as described in greater detail below with reference to FIG. 3. Such work of breathing measures determined by WOB calculation module 22 may then be communicated to graphic user interface 26 for display via display device 20.

According to the embodiment shown in FIG. 2, a ventilation system 10b for providing breathing assistance to a patient 12 may include a ventilator 14, one or more devices for connecting ventilator 14 to patient 12, and a separate WOB module 50. Ventilator 14 may include a ventilation control system 18 and a display screen 20, such as discussed above regarding the embodiment shown in FIG. 1. Ventilation control system 18 may be operable to control the ventilation support provided by ventilator 14 based on various inputs, such as inputs received from an operator and/or data received from various sensors, as discussed below. Display device 20 may be fully or partially integrated with ventilator 14 and may comprise, e.g., a touch screen display or other visual display. Display device 20 may be configured to display various information regarding the ventilation of patient 12. Display device 20 may be part of or otherwise associated with, a graphic user interface 26. In this embodiment, graphic user interface 26 may be configured to display various information via display device 20 and/or provide an interface for accepting input from human operators via display device 20 and/or other input devices (e.g., to set or modify ventilation settings, to access data, and/or to change or configure the display).

WOB module 50 may include a display device 52, a WOB calculation module 22, and any other suitable hardware or software for determining and/or displaying one or more WOB measures. For example, WOB module 50 may be configured to display a WOB graphic 16 via display device 52, e.g., a touch screen display or other visual display. As discussed above, WOB graphic 16 may be a full screen display or may occupy a portion of a display screen. In some embodiments, WOB module 50 may include a graphic user interface 54, which may be operable to display WOB graphic 16 and/or other information via display device 52 and, in some embodiments, provide an interface for accepting input from human operators via display device 52 and/or other user input devices (e.g., to set or modify various settings, access data, and/or change or configure the display).

WOB calculation module 22 may be operable to calculate or otherwise determine one or more work of breathing measures based on various input data, including data collected by sensors 40. WOB calculation module 22 may receive such input data from any suitable component of ventilation system 10b. For example, WOB module 50 may be communicatively coupled to one or more sensors 40 (e.g., sensors 40 located at or proximate to an artificial airway (e.g., an endotracheal tube or other device), a Wye connector, or breathing circuit 30) such that WOB module 50 may receive data directly from such sensors 40, e.g., as indicated by dashed line 56. Alternatively, WOB module 50 may be communicatively coupled to ventilator 14 such that WOB module 50 may receive data from ventilator 14 (e.g., as indicated by dashed line 58), which may include data received from various sensors 40 (which data may or may not be first processed or otherwise acted on by ventilator 14 and then communicated to WOB module 50). WOB calculation module 22 may receive data from sensors 40 directly or indirectly in any other suitable manner. WOB calculation module 22 may then calculate or otherwise determine one or more work of breathing measures based on such data from sensors 40, and communicate the determined work of breathing measures for display via display device 52.

It should be understood that components of ventilation systems 10a and 10b may include any hardware, software, firmware or other components suitable for providing ventilation assistance to patient 12 and/or determining and displaying one or more work of breathing measures. For example, ventilator 14 may include various processors, memory devices, user inputs, status indicators, audio devices, and/or software or other logic for providing various ventilator functions.

Figure 3:
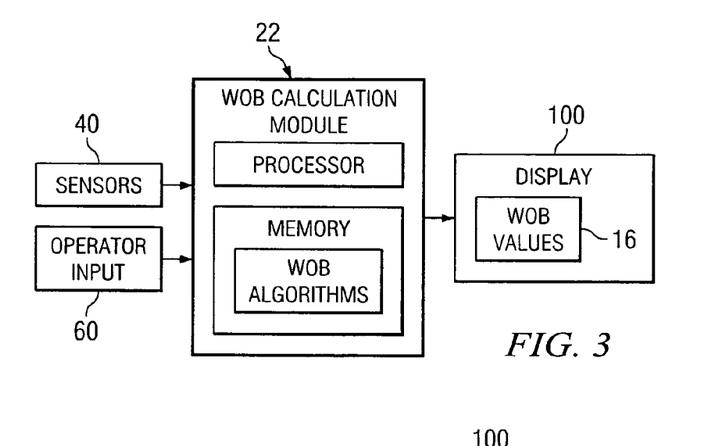
FIG. 3 is a block diagram illustrating an example system for determining and displaying work of breathing measures, according to some embodiments.

FIG. 3 is a block diagram illustrating an example system for determining and displaying work of breathing measures, according to some embodiments. As discussed above, WOB calculation module 22 may be operable to calculate or otherwise determine one or more work of breathing measures based on various input data. Such input data may include data received from sensors 40 and/or data or settings input by an operator, indicated in FIG. 3 as operator input 60. Such WOB measures may then be represented in a WOB graphic 16 displayed on any suitable display device 100, e.g., display devices 20 or 52 discussed above with reference to FIGS. 1 and 2. For example, WOB calculation module 22 may calculate measures for $WOB_{TOTAL}$, $WOB_{PATIENT}$, $WOB_{VENTILATOR}$, $WOB_{PATIENT-ELASTIC}$, and/or $WOB_{PATIENT-RESISTIVE}$. One, some, or all of these measures may then be displayed in a WOB graphic 16 in any suitable manner, e.g., using graphic and/or numeric representations.

WOB calculation module 22 may include a processor 62, memory 64, and any other suitable hardware or software. Memory 64 may store one or more WOB algorithms 66 and/or any other suitable software or logic that may be executable by processor 60 for calculating one or more work of breathing measures, e.g., as discussed below.

WOB calculation module 22 may use data collected by sensors 40 to calculate or otherwise determine work of breathing measures in any of a variety of manners. For example, in some embodiments in which a balloon is inserted in the patient's esophagus, sensors 40 may be used to monitor pressure and volume (flow*time) at the airway opening (e.g., at or proximate to a Wye connector). Such data may be communicated to WOB calculation module 22, which may determine or calculate one or more WOB measures based on such received data.

Alternatively, WOB calculation module 22 may calculate estimated WOB measures based on data monitored entirely external to the patient, e.g., using WOB 66 algorithms that use data from sensors 40 as inputs. For example, in a pressure assisted ventilation (PAV) environment, WOB calculation module 22 may receive data from sensors 40 positioned in or proximate to ventilator 14 and calculate estimated WOB measures using such data as inputs for one or more suitable PAV algorithms. Example techniques for providing or generating PAV, which may lead to WOB calculations, are disclosed in U.S. Pat. No. 5,107,830, which is hereby incorporated by reference in its entirety. In addition, example techniques for determining or approximating resistance and/or elastance in a PAV environment, which may be used in calculating WOB values, are disclosed in U.S. Pat. No. 5,884,622 and U.S. Pat. No. 6,837,242, which are hereby incorporated by reference in their entirety.

Thus, in some embodiments, WOB calculation module 22 may include or use such techniques and/or other known techniques for calculating estimated WOB measures, which may then be displayed via WOB graphic 16. It should be understood that WOB measures may be measured, estimated, or otherwise determined in any other suitable manner in both PAV and non-PAV environments.

Various example embodiments of WOB graphic 16 are illustrated in FIGS. 4-9, as discussed in greater detail below. WOB graphic 16 may be displayed on any suitable display device 100, e.g., display devices 20 or 52 discussed above with reference to FIGS. 1 and 2. Although the present disclosure discusses the generation and/or display of a WOB graphic in connection with a ventilator, it should be understood that the disclosed WOB graphics may similarly be used in connection with other stand-alone systems or devices that calculate WOB measures.

WOB graphic 16 may comprise, e.g., a graphic on a general-purpose display screen or on a dedicated display or display device, and may be configured to provide a user-friendly display that represents a patient's work of breathing. However, display device 100 may additionally or alternatively be operable to visually represent patient data, alarm conditions, various charts, graphs, tables, and/or other such information as may be appropriate or useful to a caregiver in assessing a patient's respiratory or other vital functions. For example, the display of display device 100 may be divided into multiple sections, with one section displaying the WOB graphic 16 while one or more other sections display various other items such as ventilator parameters, patient data, etc. However, such information may alternatively be displayed in a non-sectored layout, e.g., intermingled or integrated with the WOB graphic 16.

As discussed above, WOB graphic 16 may indicate the total work of breathing ($WOB_{TOTAL}$), the patient's work of breathing ($WOB_{PATIENT}$), and/or the components of the patient's WOB—an elastic WOB component ($WOB_{PATIENT-ELASTIC}$) and a resistive WOB component ($WOB_{PATIENT-RESISTIVE}$). In some embodiments, WOB graphic 16 may include a scale having any suitable shape or configuration (e.g., a linear scale, a circular or semicircular scale, or an elliptical scale) and one or more indicators that move relative to the scale to indicate one or more work of breathing parameters. For example, WOB graphic 16 may include a $WOB_{TOTAL}$ indicator that moves relative to the scale to represent a measure of $WOB_{TOTAL}$, and a $WOB_{PATIENT}$ indicator that moves relative to the scale to represent a measure of $WOB_{PATIENT}$. The scale may be divided into sectors that generally correspond to different work of breathing levels. The sectors may be visibly discernable from each other (or at least from immediately adjacent sectors).

The elastic-resistive WOB graphic may be divided into a first portion and a second portion, the first portion indicating the elastic WOB component ($WOB_{PATIENT-ELASTIC}$) and the second portion indicating the resistive WOB component ($WOB_{PATIENT-RESISTIVE}$). The overall size of the elastic-resistive WOB graphic may remain constant as the relative sizes of the first and second portions dynamically adjust to indicate a measure of the elastic WOB component relative to a measure of the resistive WOB component.

Each work of breathing measure (e.g., $WOB_{TOTAL}$, $WOB_{PATIENT}$, $WOB_{VENTILATOR}$, $WOB_{PATIENT-ELASTIC}$, and/or $WOB_{PATIENT-RESISTIVE}$) may be calculated and/or displayed using any suitable units or other parameter. For example, each WOB measure may be calculated and/or displayed as Joules (J), Joules per liter (J/L), Joules per minute (J/min) (i.e., power), or Joules per liter per kilogram (J/L/kg) (i.e., normalized power). Thus, it should be understood that the following discussion of WOB measures displayed in J/L is exemplary only.

Figure 4:
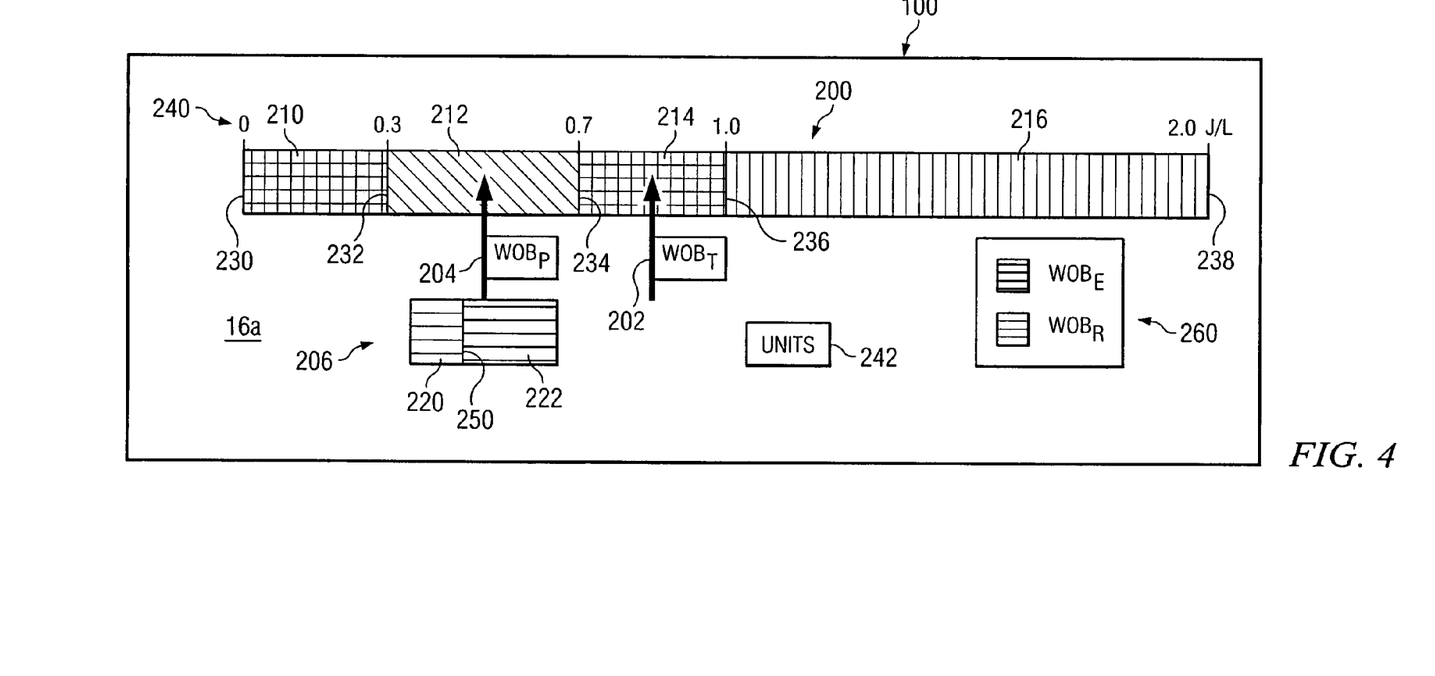
FIG. 4 illustrates a first example graphic work of breathing graphic, according to one embodiment of the disclosure.

FIG. 4 illustrates an example of a WOB graphic 16a on a display device 100, according to one embodiment of the disclosure. WOB graphic 16a may include a scale 200, a $WOB_{TOTAL}$ indicator 202 for indicating a measure of the total WOB, a $WOB_{PATIENT}$ indicator 204 for indicating a measure of the patient's WOB, and/or an elastic-resistive WOB indicator 206 for indicating the elastic and resistive WOB components of the patient's WOB. scale 200 may be divided into a plurality of sectors that may generally correspond to different levels of acceptability, desirability, or safety regarding the patient's breathing. For example, such sectors may include at least one first sector representing a sub-normal work of breathing range, at least one second sector representing a normal work of breathing range, and at least one third sector representing a supra-normal work of breathing range. As another example, such sectors may include at least one first sector representing a sub-normal work of breathing range, at least one second sector representing a normal work of breathing range, at least one third sector representing a supra-normal work of breathing range, and at least one fourth sector representing a cautionary supra-normal work of breathing range.

In the example shown in FIG. 4, scale 200 may include four sectors, 210, 212, 214, and 216, which correspond to a sub-normal work of breathing range (sector 210), a normal work of breathing range (sector 212), a supra-normal work of breathing range (sector 214), and a cautionary supra-normal work of breathing range (sector 216). Sub-normal sector 210 may represent a range in which the patient's WOB may be below an appropriate level for administering a proper respiratory management protocol. Normal sector 212 may represent a range in which the patient's contributed WOB may be within an appropriate level for administering a proper respiratory management protocol. Supra-normal sector 214 may represent a range in which the patient's WOB may be above an appropriate level for administering a proper respiratory management protocol. Cautionary supra-normal sector 216 may represent a range in which the patient's WOB may be at a potentially harmful level. It should be understood that in other embodiments, WOB graphic 16a may include any number and/or type(s) of sectors corresponding to any various conditions.

$WOB_{TOTAL}$ indicator 202 may comprise any pointer or other graphic that may advance and retreat along scale 200 as the $WOB_{TOTAL}$ changes over time (e.g., when a "percent support" setting is adjusted in a PAV ventilation environment). $WOB_{TOTAL}$ indicator 202 may include any suitable label or other identifier. In some embodiments, $WOB_{TOTAL}$ indicator 202 may include a numerical indication of the current $WOB_{TOTAL}$ measure. In other embodiments, no such numerical indication is displayed.

Similarly, $WOB_{PATIENT}$ indicator 204 may comprise any pointer or other graphic that may advance and retreat along scale 200 as the $WOB_{PATIENT}$ changes over time. $WOB_{PATIENT}$ indicator 204 may include any suitable label or other identifier. In some embodiments, $WOB_{PATIENT}$ indicator 204 may include a numerical indication of the current $WOB_{PATIENT}$ measure. In other embodiments, no such numerical indication is displayed.

Elastic-resistive WOB indicator 206 may be divided into a first indicator portion 220 representing a measure of $WOB_{PATIENT-ELASTIC}$, and a second indicator portion 222 representing a measure of $WOB_{PATIENT-RESISTIVE}$. The relative sizes of first and second indicator portions 220 and 222 may adjust dynamically as the relative measures of $WOB_{PATIENT-ELASTIC}$ and $WOB_{PATIENT-RESISTIVE}$ change over time. In some embodiments (e.g., as such as shown in FIG. 4), elastic-resistive WOB indicator 206 may be coupled to or otherwise associated with $WOB_{PATIENT}$ indicator 202, such that elastic-resistive WOB indicator 206 advances and retreats along scale 200 in coordination with $WOB_{PATIENT}$ indicator 202.

In this embodiment, scale 200 is oriented horizontally and $WOB_{TOTAL}$ indicator 202, $WOB_{PATIENT}$ indicator 204, and elastic-resistive WOB indicator 206 move horizontally along scale 200. In other embodiments, scale 200 may be oriented, and indicators 202, 204, and/or 206 may move, in any other direction (e.g., vertically, diagonally, in a stepped manner, or in a curved manner). Indicators 202, 204, and/or 206 may be positioned relative to scale 200 in any suitable manner. For example, 202, 204, and/or 206 may be positioned on the same side of scale 200 or on opposite sides of scale 200. As another example, one or more of indicators 202, 204, and/or 206 may be partially or fully superimposed over scale 200 and may advance or retreat along or through sectors 210-216 to indicate one or more work of breathing measures. Further, scale 200 and indicators 202, 204, and/or 206 may be positioned anywhere on WOB graphic 16a.

In some embodiments, sector transition lines may divide the respective sectors of WOB scale 200. For example, as shown in FIG. 4, sector transition lines 230, 232, 234, 236, and 238 may divide sectors 210-216. Sector transition lines 230-238 may have any suitable shape and orientation. For example, sector transition lines 230-238 may be shaped to mirror or correspond to the shape or form of one or both ends of elastic-resistive WOB indicator 206. In other embodiments, scale 200 may not include sector transition lines.

In some embodiments, sectors 210-216 may be visibly discernable from each other, or at least from immediately adjacent sectors. For example, sectors 210-216 may be color-coded, shaded, or differently shaped such that sectors 210-216 may be visibly distinguishable from each other. Such color coding is represented in FIG. 4 by different levels of shading.

In an example embodiment, sector 210 may be color-coded yellow, sector 92 may be color-coded green, sector 94 may be color-coded yellow, and sector 96 may be color-coded orange, which may be commensurate with good human factors. It should be understood that any coloring may be chosen for each respective sector. Such color-coding may be permit the caregiver to quickly and easily determine the location of indicators 202, 204, and/or 206 along scale and/or provide the caregiver a quick indication of the status of the ventilatory support. In other embodiments, one, some or all of sectors 210-216 may be free from color-coding or other types of fill.

Elastic-resistive WOB indicator 206 may have any suitable shape and/or configuration. For example, elastic-resistive WOB indicator 206 may comprise a box, as shown in FIG. 4, or may take the form of a bar graph, a vertically-oriented line segment, or any other suitable symbol or graphic representation that may advance and retreat along sectors 210-216 to indicate measures of $WOB_{PATIENT-ELASTIC}$ and/or $WOB_{PATIENT-RESISTIVE}$. For example, in one embodiment, elastic-resistive WOB indicator 206 comprises a bar or other graphic that expands in length along scale 200 to indicate a measure of $WOB_{PATIENT}$. The bar or other graphic may be divided into indicator portions 220 and 222 that may adjust dynamically to indicate measures of $WOB_{PATIENT-ELASTIC}$ and $WOB_{PATIENT-RESISTIVE}$ over time. In some embodiments (e.g., where elastic-resistive WOB indicator 206 is superimposed over scale 200), the height of elastic-resistive WOB indicator 206 (in the vertical direction as shown in FIG. 4) may be less than the height of scale 200, which may increase the visual contrast between elastic-resistive WOB indicator 206 and scale 200.

In some embodiments, the overall (or exterior) size and/or shape of elastic-resistive WOB indicator 206 remain constant, while the relative sizes of component portions 220 and 222 adjust dynamically. In other embodiments, the overall (or exterior) size and/or shape of elastic-resistive WOB indicator 206 may change over time. For example, in embodiments in which elastic-resistive WOB indicator 206 comprises a bar graph (e.g., extending from the left edge of scale 200), the horizontal length of elastic-resistive WOB indicator 206 may be dynamic.

In some embodiments, scale 200 may include a set of numerical indices 240 to quantify the range of WOB values for each sector 210-216. Such values may have any suitable units, e.g., Joules (J), Joules per liter (J/L), Joules per minute (J/min) (i.e., power), or Joules per minute per kilogram (J/min/kg) (i.e., normalized power). The particular values defined by numerical indices 240 (and thus, the ranges of each sector 210-216) may be determined based on any suitable data, e.g., historical data. In some embodiments, the values defined by numerical indices 240 may be permanent for WOB graphic 16a. In other embodiments, the values defined by numerical indices 240 may be configurable and/or adjustable by an operator. In addition, different numerical indices 240 having different values may be used for different patients, different respiratory management protocols, or for any other varying parameter(s).

One example set of numerical indices 240 is shown in FIG. 4. In this example, suppose that a normal acceptable range for a patient's WOB ($WOB_{PATIENT}$) is typically 0.3 J/L to 0.7 J/L. Thus, the range from 0 J/L to 0.3 J/L may be deemed subnormal. Thus, unless there are particular reasons for allowing a patient's WOB to fall below 0.3 J/L, a $WOB_{PATIENT}$ reading consistently remaining below 0.3 J/L could signal to the caregiver that the patient's management protocol should be reconsidered. Further, suppose that values falling above 0.70 J/L are generally above an acceptable level. Thus, unless there are particular reasons for allowing a patient's WOB to rise above 0.7 J/L, a $WOB_{PATIENT}$ reading consistently remaining above 0.7 J/L could signal to the caregiver that the patient's management protocol should be reconsidered. Further, suppose that values falling above 1.0 J/L are deemed to be particularly cautionary or potentially harmful. Thus, unless there are particular reasons for allowing a patient's WOB to rise above 1.0 J/L, a $WOB_{PATIENT}$ reading consistently remaining above 1.0 J/L could signal to the caregiver that the patient's management protocol is particular cautionary or potentially harmful and should thus be reconsidered.

Thus, in this example, the set of numerical indices 240 includes the values 0, 0.3, 0.7, 1.0, and 2.0 positioned proximate the corresponding sector transition lines 230-238. A graphic representation of the unit of measurement, e.g., Joules/liter (J/L), may be included, as shown in FIG. 4, or may be omitted. Numerical indices 240 may be otherwise positioned and/or configured to correspond to appropriate sector transitions or other points within sectors 210-216 of WOB graphic 16a.

In some embodiments, WOB graphic 16a may include a WOB units selector 242 (e.g., a button) providing an interface allowing an operator to select from multiple units for which to display WOB measures on WOB graphic 16a. For example, selecting button 242 may open a window allowing the user to select from different units—e.g., Joules (J), Joules per liter (J/L), Joules per minute (J/min), or Joules per minute per kilogram (J/min/kg)—for which WOB measures are displayed in WOB graphic 16a. When an operator selects a particular unit, the values and/or units displayed in numerical indices 240 may be automatically update as appropriate. In this manner, this operator may select a desired units setting for WOB measures displayed in WOB graphic 16a.

Like scale 200, elastic-resistive WOB indicator 206 may be configured such that indicator portions 220 and 222 are visibly discernable from each other, such that a caregiver can quickly and easily identify the relative magnitudes of $WOB_{PATIENT-ELASTIC}$ and $WOB_{PATIENT-RESISTIVE}$. In some embodiments, indicator portions 220 and 222 are shaded in two different colors (or two different shades of the same basic color). However, it should be understood that indicator portions 220 and 222 may be otherwise colored or shaded, or may not be colored or shaded at all.

Indicator portions 220 and 222 may be divided by a reader 250, which may dynamically move within elastic-resistive WOB indicator 206 (e.g., to the left or right) to adjust the relative sizes of indicator portions 220 and 222 as the relative magnitude and/or percentage of the resistive and elastic WOB components change over time. In some embodiments, reader 250 may double as, or be otherwise associated with $WOB_{PATIENT}$ indicator 204. In other embodiments, reader 250 may be distinct from $WOB_{PATIENT}$ indicator 204. In other embodiments, a leading or trailing line of elastic-resistive WOB indicator 206, or any other appropriate graphic representation within or associated with elastic-resistive WOB indicator 206, may serve as $WOB_{PATIENT}$ indicator 204. For example, the leading end (here, the right-most boundary or indicator portion 222) may serve as $WOB_{PATIENT}$ indicator 204.

In other embodiments, elastic-resistive WOB indicator 206 may simply comprise a line or other suitable indicating means, and the patient's resistive and/or elastic WOB components may be graphically displayed separately, as numerical values of an appropriate unit of measure, or in any other suitable manner.

In some embodiments of the present disclosure, the caregiver may be able to easily identify the relative percentages of the patient's resistive work and elastic work from indicator portions 220 and 222, respectively, of elastic-resistive WOB indicator 206. By dividing elastic-resistive WOB indicator 206 into resistive and elastic WOB components 220 and 222, a caregiver may be able to easily determine whether a patient is exerting too much or too little resistive or elastic work, which in turn may assist the caregiver in diagnosing the patient's condition and/or adjusting the ventilation strategy.

Figure 6:
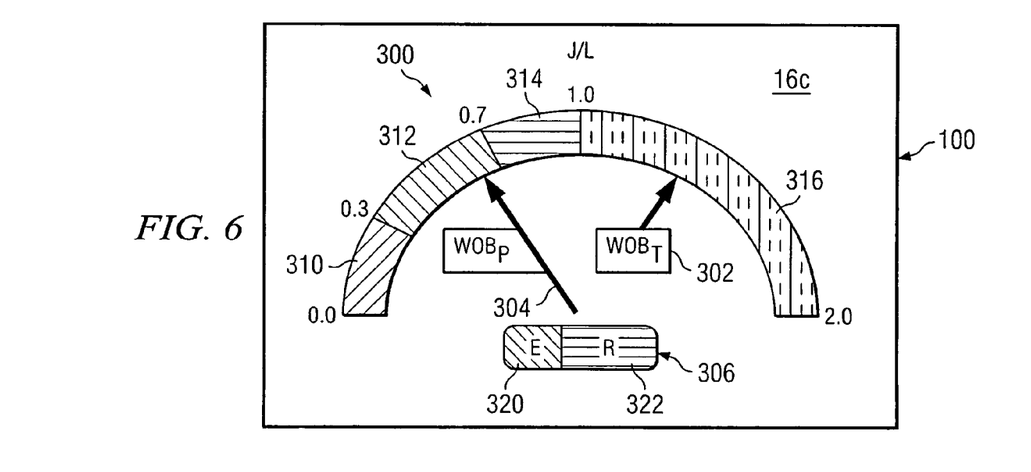
FIG. 6 illustrates a third example graphic work of breathing graphic, according to another embodiment of the disclosure.

In some embodiments, WOB graphic 16a may include one or more display legends that may include any desired graphical representations to assist the caregiver in better understanding WOB graphic 16a. For example, as shown in FIG. 4, a display legend 260 may indicate that indicator portions 220 and 222 of elastic-resistive WOB indicator 206 represent the elastic WOB component (illustrated as "$WOB_E$") and the resistive WOB component (illustrated as "$WOB_R$"), respectively, of the patient's WOB. In other embodiments, symbols or legends indicating that indicator portions 220 and 222 represent the elastic and resistive WOB components may be located in or adjacent indicator portions 220 and 222 (such as shown in the embodiment of FIG. 6, for example). Similarly, display legend 260 or another display legend may explain the color-coding of sectors 210-216 of scale 200.

Figure 5:
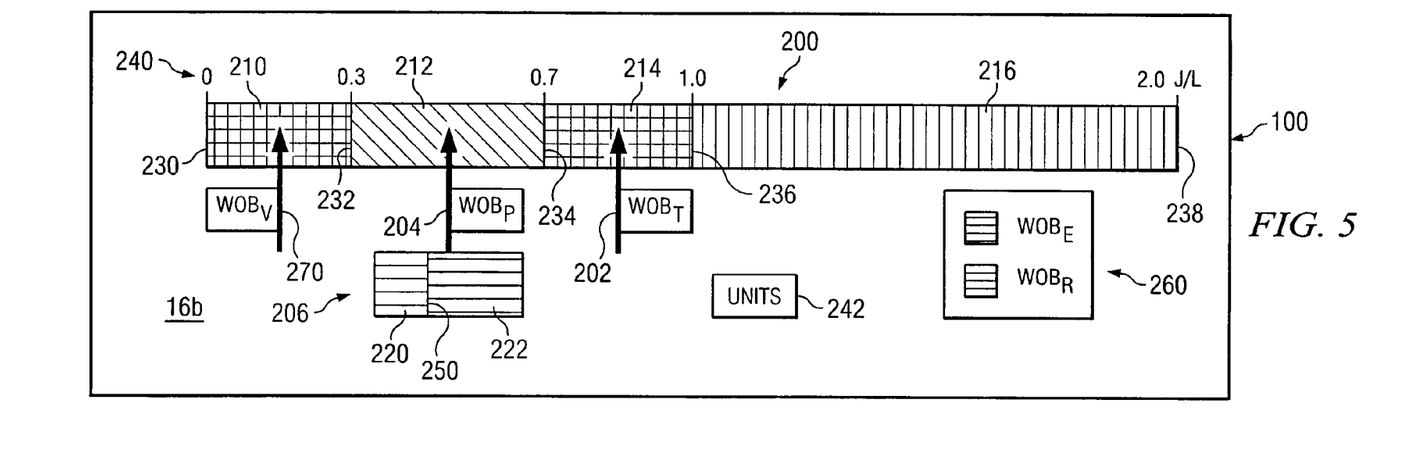
FIG. 5 illustrates a second example graphic work of breathing graphic, according to one embodiment of the disclosure.

FIG. 5 illustrates another example of a WOB graphic 16b on a display device 100, according to one embodiment of the disclosure. WOB graphic 16b may be similar to WOB graphic 16a shown in FIG. 4 and discussed above, but may additionally include a $WOB_{VENTILATOR}$ indicator 270 that indicates a measure of the ventilator's WOB. $WOB_{VENTILATOR}$ indicator 270 may comprise any pointer or other graphic that may advance and retreat along scale 200 as the $WOB_{VENTILATOR}$ changes over time. $WOB_{VENTILATOR}$ indicator 270 may include any suitable label or other identifier. In some embodiments, $WOB_{VENTILATOR}$ indicator 270 may include a numerical indication of the current $WOB_{VENTILATOR}$ measure. In other embodiments, no such numerical indication is displayed.

FIG. 6 illustrates another example of a WOB graphic 16c on a display device 100, according to another embodiment of the disclosure. WOB graphic 16c may include a scale 300, a $WOB_{TOTAL}$ indicator 302 for indicating a measure of the total WOB, a $WOB_{PATIENT}$ indicator 304 for indicating a measure of the patient's WOB, and/or an elastic-resistive WOB indicator 306 for indicating the elastic and resistive WOB components of the patient's WOB.

Scale 300 and indicators 302-306 may be analogous to scale 200 and indicators 202-206 shown in FIG. 4. Scale 300 may extend in an arc, and may be divided into sections 310-316, which may be similar to sections 210-216 discussed above. $WOB_{TOTAL}$ indicator 302 may comprise a pointer that rotates relative to curved scale 300 to indicate a measure of the total WOB. Similarly, $WOB_{PATIENT}$ indicator 304 may comprise a pointer that rotates relative to curved scale 300 to indicate a measure of the patient's WOB.

Elastic-resistive WOB indicator 306 may be divided into indicator portions 320 and 322, which may indicate the elastic and resistive WOB components of the patient's WOB, e.g., as discussed above regarding indicator portions 220 and 222 of elastic-resistive WOB indicator 206. The relative sizes (e.g., the length and/or width) of indicator portions 320 and 322 may dynamically change to indicate the current relative measures of elastic and resistive WOB components, e.g., as discussed above regarding elastic-resistive WOB indicator 206. However, unlike elastic-resistive WOB indicator 206, elastic-resistive WOB indicator 306 may remain stationary (rather than moving along scale 300). In addition, in some embodiments, an indication that indicator portions 320 and 322 represent the elastic and resistive WOB components is located in or adjacent indicator portions 320 and 322. For example, as shown in FIG. 6, the letters "E" and "R" may be displayed in indicator portions 320 and 322 to indicate that that indicator portions 320 and 322 represent the elastic and resistive WOB components, respectively. In other embodiments, WOB graphic 16c may include one or more display legends to provide such information, e.g., as discussed above regarding display legend 260.

Figure 7:
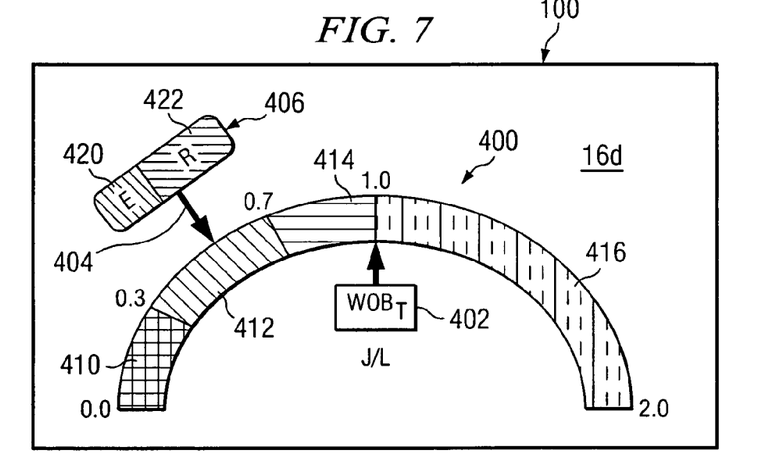
FIG. 7 illustrates a fourth example graphic work of breathing graphic, according to another embodiment of the disclosure.

FIG. 7 illustrates another example of a WOB graphic 16d on a display device 100, according to another embodiment of the disclosure. WOB graphic 16d may include a scale 400, a $WOB_{TOTAL}$ indicator 402 for indicating a measure of the total WOB, a $WOB_{PATIENT}$ indicator 404 for indicating a measure of the patient's WOB, and/or an elastic-resistive WOB indicator 406 for indicating the elastic and resistive WOB components of the patient's WOB. Scale 400 and indicators 402-406 may be analogous to scale 300 and indicators 302-306 shown in FIG. 6. For example, scale 400 may extend in an arc, and may be divided into sections 410-416. $WOB_{TOTAL}$ indicator 402 may move in an arced path along an inner perimeter of scale 400. In other embodiments, $WOB_{TOTAL}$ indicator 402 may move along an outer perimeter of scale 400. $WOB_{PATIENT}$ indicator 404 may move in an arced path along an outer scale 400, and may be coupled to elastic-resistive WOB indicator 406 such that elastic-resistive WOB indicator 406 moves along with $WOB_{PATIENT}$ indicator 404. In other embodiments, elastic-resistive WOB indicator 406 and/or $WOB_{PATIENT}$ indicator 404 may move along an inner perimeter of scale 400.

Elastic-resistive WOB indicator 406 may be divided into indicator portions 420 and 422, which may indicate the elastic and resistive WOB components of the patient's WOB. The relative sizes of indicator portions 420 and 422 may dynamically change to indicate the current relative measures of elastic and resistive WOB components, e.g., as discussed above regarding elastic-resistive WOB indicator 206. In addition, in some embodiments, an indication (e.g., the letters "E" and "R") that indicator portions 420 and 422 represent the elastic and resistive WOB components may be located in or adjacent indicator portions 420 and 422, such as discussed above regarding FIG. 6.

Figure 8:
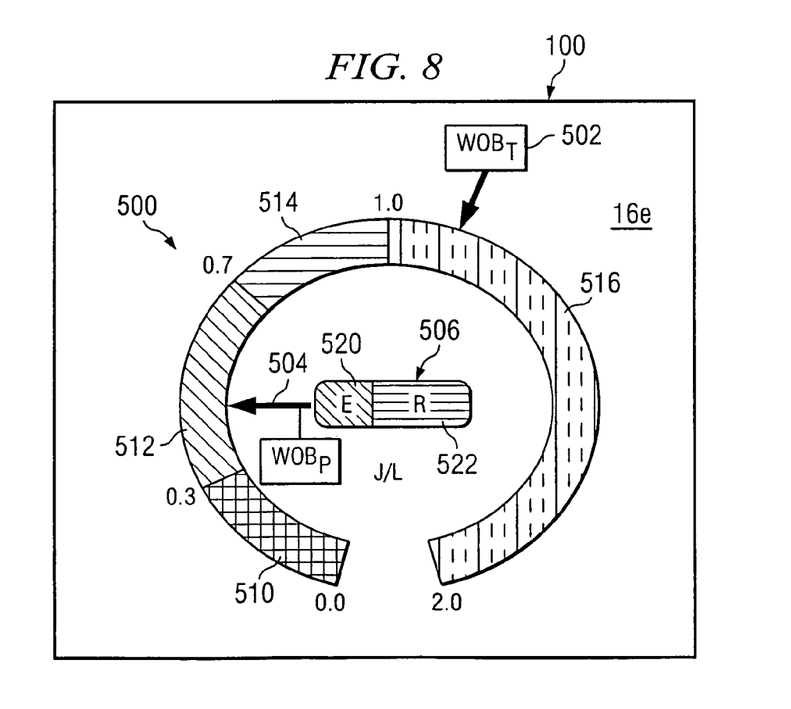
FIG. 8 illustrates a fifth example graphic work of breathing graphic, according to another embodiment of the disclosure.

FIG. 8 illustrates another example of a WOB graphic 16e on a display device 100, according to another embodiment of the disclosure. WOB graphic 16e may include a scale 500, a $WOB_{TOTAL}$ indicator 502 for indicating a measure of the total WOB, a $WOB_{PATIENT}$ indicator 504 for indicating a measure of the patient's WOB, and/or an elastic-resistive WOB indicator 506 for indicating the elastic and resistive WOB components of the patient's WOB. Scale 500 and indicators 502-506 may be analogous to scale 200 and indicators 202-206 shown in FIG. 4. Scale 500 may extend in an elliptical or other curved shape, and may be divided into sections 510-516. $WOB_{TOTAL}$ indicator 502 may move in a curved path along an outer perimeter of scale 500. In other embodiments, $WOB_{TOTAL}$ indicator 502 may move along an inner perimeter of scale 500. $WOB_{PATIENT}$ indicator 504 may move in a curved path along an inner scale 500. In other embodiments, $WOB_{PATIENT}$ indicator 504 may move along an outer perimeter of scale 500.

Elastic-resistive WOB indicator 506 may be divided into indicator portions 520 and 522, which may indicate the elastic and resistive WOB components of the patient's WOB. The relative sizes of indicator portions 520 and 522 may dynamically change to indicate the current relative measures of elastic and resistive WOB components. Like elastic-resistive WOB indicator 306 shown in FIG. 6, elastic-resistive WOB indicator 506 may remain stationary (rather than moving along scale 500). As discussed above, an indication (e.g., the letters "E" and "R") that indicator portions 520 and 522 represent the elastic and resistive WOB components may be located in or adjacent indicator portions 520 and 522.

Figure 9:
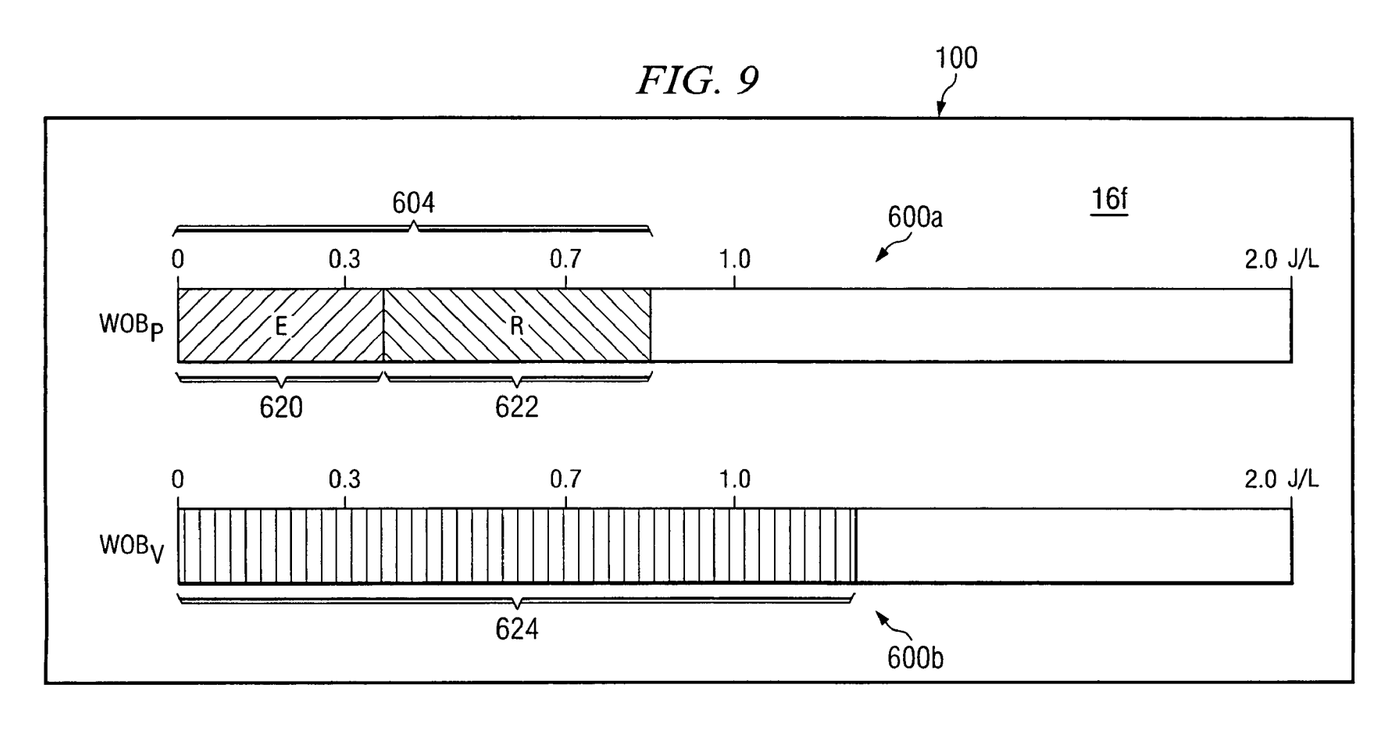
FIG. 9 illustrates a sixth example graphic work of breathing graphic, according to another embodiment of the disclosure.

FIG. 9 illustrates another example of a WOB graphic 16f on a display device 100, according to another embodiment of the disclosure. WOB graphic 16f may include one or more scales for indicating the patient's WOB ($WOB_{PATIENT}$), the ventilator's WOB (WOB$_{VENTILATOR}$), and/or the total WOB (WOB$_{TOTAL}$). For example, as shown in FIG. 9, WOB graphic 16f may include (a) a first scale 600a for indicating the patient's WOB (WOB$_{PATIENT}$) and/or the elastic and resistive WOB components of WOB$_{PATIENT}$, and (b) a second scale 600b for indicating the ventilator's WOB (WOB$_{VENTILATOR}$). In another embodiment, WOB graphic 16f may include a third scale for indicating the total WOB (WOB$_{TOTAL}$). In other embodiments, WOB graphic 16f may include any one, two or all three of such scales indicating WOB$_{PATIENT}$, WOB$_{VENTILATOR}$, and/or WOB$_{TOTAL}$.

Regarding scale 600a shown in FIG. 9, a WOB$_{PATIENT}$ indicator 604 in the form of a bar may advance and retreat along scale 600a to indicate a measure of the patient's WOB, WOB$_{PATIENT}$. WOB$_{PATIENT}$ indicator 604 may be divided into indicator portions 620 and 622, which may indicate the elastic and resistive WOB components of the patient's WOB, respectively. The sizes of indicator portions 620 and 622 may dynamically change to indicate the current relative measures of elastic and resistive WOB components. An indication (e.g., the letters "E" and "R") that indicator portions 620 and 622 represent the elastic and resistive WOB components may be located in or adjacent indicator portions 620 and 622. Alternatively, WOB graphic 16f may include legend (e.g., as discussed above with respect to FIG. 4) to indicate that portions 620 and 622 represent the elastic and resistive WOB components of the patient's WOB. Indicator portions 620 and 622 may be color-coded or otherwise visually distinct, e.g., as described above. Scale 600a may include a set of numerical indices (e.g., similar to numerical indices 240 shown in FIG. 4) to quantify ranges of WOB values for pre-determined sectors of scale 600a (e.g., 0 to 0.3, 0.3 to 0.7, 0.7 to 1.0, and 1.0 to 2.0).

Regarding scale 600b, a WOB$_{VENTILATOR}$ indicator 624 in the form of a bar may advance and retreat along scale 600b to indicate a measure of the ventilator's WOB, WOB$_{VENTILATOR}$. WOB$_{VENTILATOR}$ indicator 624 may be color-coded or otherwise visually distinct from indicator portions 620 and 622 of WOB$_{PATIENT}$ indicator 604. In other embodiments, WOB graphic 16f may not include scale 600b or WOB$_{VENTILATOR}$ indicator 624. Like scale 600a, scale 600b may include a set of numerical indices to quantify ranges of WOB values for pre-determined sectors of scale 600b. In other embodiments, scales 600a and 600b may share a common set or numerical indices, or may not include numerical indices.

Although the disclosed embodiments have been described in detail, it should be understood that various changes, substitutions and alterations can be made herein without departing from the spirit and scope of the disclosure as illustrated by the following claims.

What is claimed is:

1. A breathing support system, comprising:
   a breathing support device configured to deliver gas to a patient;
   a software-generated image representing a work of breathing graphic indicating one or more work of breathing measures regarding the patient's breathing, wherein the one or more work of breathing measures include an elastic work of breathing component and a resistive work of breathing component;
   a software-generated image representing an elastic work of breathing indicator indicating a measure of the elastic work of breathing component;
   a software-generated image representing a resistive work of breathing indicator indicating a measure of the resistive work of breathing component; and
   a display device associated with the breathing support device, the display device configured to display the software-generated images,
   wherein the software-generated image representing the work of breathing graphic includes:
   a software-generated image representing a scale; and
   one or more software-generated images representing work of breathing indicators that move relative to the software-generated image representing the scale to indicate the one or more work of breathing measures.

2. The system according to claim 1, further comprising a work of breathing calculation module configured to receive data from one or more sensors and calculate the one or more work of breathing measures using one or more work of breathing algorithms.

3. The system according to claim 2, wherein the data received by the work of breathing calculation module comprises data regarding delivery of the gas to the patient, including at least one of pressure and flow of the gas delivered to the patient.

4. The system according to claim 2, wherein the work of breathing calculation module is configured to receive the data from the one or more sensors associated with an artificial airway inserted in the patient.

5. The system according to claim 1, further comprising:
   one or more sensors configured to obtain data regarding the patient's breathing;
   a memory device storing one or more work of breathing algorithms; and
   a processor communicatively coupled to the one or more sensors and the memory device and configured to determine the one or more work of breathing measures based at least on the data obtained by the one or more sensors and the one or more work of breathing algorithms.

6. The system according to claim 5, wherein the one or more sensors are associated with an artificial airway inserted in the patient.

7. The system according to claim 5, wherein the one or more sensors are not associated with an artificial airway inserted in the patient.

8. The system according to claim 1, wherein the display device is at least partially integrated with the breathing support device.

9. The system according to claim 1, wherein the display device is physically separate from the breathing support device.

10. The system according to claim 1, wherein the software-generated image representing the work of breathing graphic includes:
   a software-generated image representing a total work of breathing indicator indicating a measure of a total work of breathing for the patient's breathing, the total work of breathing comprising a patient work of breathing component and a device work of breathing component, the patient work of breathing component comprising the portion of the total work of breathing provided by a patient and the device work of breathing component comprising a portion of the total work of breathing provided by the breathing support device.

11. The system according to claim 1, wherein the software-generated image representing the work of breathing graphic further includes a software-generated image representing an indication of the elastic work of breathing component relative to the resistive work of breathing component.

12. The display according to claim 1, wherein the one or more work of breathing measures comprise one or more estimated measures.

13. The system according to claim 1, wherein the software-generated image representing the work of breathing graphic includes:

a software-generated image representing an elastic-resistive work of breathing indicator indicating the measure of the elastic work of breathing component relative to the measure of the resistive work of breathing component.

14. The system according to claim 1, wherein the work of breathing graphic includes:

a software-generated image representing an elastic-resistive work of breathing graphic including a software-generated image representing a first portion and a software-generated image representing a second portion, the first portion indicating the measure of the elastic work of breathing component and the second portion indicating the measure of the resistive work of breathing component; and wherein relative sizes of the first and second portions of the elastic-resistive work of breathing graphic dynamically adjust to indicate the measure of the elastic work of breathing component relative to the measure of the resistive work of breathing component.

15. The system according to claim 14, wherein a size of the elastic resistive work of breathing graphic remains constant as the relative sizes of the first and second portions dynamically adjust.

16. A breathing support system, comprising:

a breathing support device configured to deliver gas to a patient;

a software-generated image representing a work of breathing graphic indicating one or more work of breathing measures regarding the patient's breathing, wherein the one or more work of breathing measures include an elastic work of breathing component and a resistive work of breathing component;

a software-generated image representing an elastic work of breathing indicator indicating a measure of the elastic work of breathing component;

a software-generated image representing a resistive work of breathing indicator indicating a measure of the resistive work of breathing component; and a display device associated with the breathing support device, the display device configured to display the software-generated images, and wherein the software-generated image representing the work of breathing graphic includes:

a software-generated image representing a patient's work of breathing indicator indicating a measure of the patient's work of breathing, the patient's work of breathing comprising a work of breathing provided by the patient, patient's work of breathing comprising a patient elastic work of breathing component and a patient resistive work of breathing component;

the software-generated image representing the elastic work of breathing indicator indicating the measure of the patient elastic work of breathing component;

the software-generated image representing the resistive work of breathing indicator indicating the measure of the patient resistive work of breathing component; and a software-generated image representing a scale, wherein the software-generated image representing the patient's work of breathing indicator dynamically moves relative to the software-generated image representing the scale to indicate the measure of the patient's work of breathing, and wherein the software-generated image representing the elastic work of breathing indicator and the software-generated image representing the resistive work of breathing indicator move along with the software-generated image representing the patient's work of breathing indicator relative to the scale.

* * * * *